United States Patent
Brom et al.

(10) Patent No.: US 10,751,516 B2
(45) Date of Patent: Aug. 25, 2020

(54) ARRANGEMENT FOR IMPLEMENTING KISSING BALLOONS FOR SIMULATING A BIFURCATED VESSEL, A KIT, A METHOD OF MANUFACTURING THE ARRANGEMENT AND A CATHETER PROVIDED WITH A BUFFER VOLUME

(71) Applicant: CAR Holding B.V., Maastricht (NL)

(72) Inventors: Henri Lorenzo Frederik Brom, Aerdenhout (NL); Alexander Cornelis De Vries, Rotterdam (NL)

(73) Assignee: CAR HOLDING B.V., Maastricht (NL)

( * ) Notice: Subject to any disclaimer, the term of this patent is extended or adjusted under 35 U.S.C. 154(b) by 1138 days.

(21) Appl. No.: 14/363,088

(22) PCT Filed: Dec. 7, 2012

(86) PCT No.: PCT/NL2012/050863
§ 371 (c)(1),
(2) Date: Jun. 5, 2014

(87) PCT Pub. No.: WO2013/085388
PCT Pub. Date: Jun. 13, 2013

(65) Prior Publication Data
US 2015/0005802 A1  Jan. 1, 2015

Related U.S. Application Data

(60) Provisional application No. 61/567,706, filed on Dec. 7, 2011.

(30) Foreign Application Priority Data

Dec. 7, 2011 (EP) .................................... 11192469

(51) Int. Cl.
*A61B 17/32* (2006.01)
*A61M 25/10* (2013.01)
(Continued)

(52) U.S. Cl.
CPC ......... *A61M 25/1011* (2013.01); *A61F 2/954* (2013.01); *A61F 2/958* (2013.01);
(Continued)

(58) Field of Classification Search
CPC .. A61M 2025/1045; A61M 2025/1052; A61M 2025/1056; A61M 25/10;
(Continued)

(56) References Cited

U.S. PATENT DOCUMENTS 6,306,177 B1   10/2001  Felt et al.
6,325,826 B1 *  12/2001  Vardi .................. A61F 2/82
                                                 623/1.15
(Continued)

FOREIGN PATENT DOCUMENTS

EP   0667131    8/1995
EP   1266629   12/2002
(Continued)

*Primary Examiner* — Elizabeth Houston
*Assistant Examiner* — Socrates L Boutsikaris
(74) *Attorney, Agent, or Firm* — Hoffmann & Baron, LLP

(57) ABSTRACT

The invention relates to an arrangement (10) for implementing kissing balloons simulating a bifurcated vessel, comprising a first catheter (4) having a first inflatable balloon (6) at or near its distal portion, a second catheter (7) having a second inflatable balloon (7a) at or near its distal portion, wherein the first catheter comprises a holding element (4) provided on the said first balloon (6), the said holding element (4) being adapted for: allowing the distal portion of the second catheter (7) to pass there through; affixing the second catheter (7) in a proximal vicinity to the first catheter (4) so that, in use, respective facing surfaces of the inflated first balloon (6) and the inflated second balloon (7a) touch each other.

16 Claims, 4 Drawing Sheets

(51) Int. Cl.
  *A61F 2/958* (2013.01)
  *A61F 2/954* (2013.01)
  *A61M 29/02* (2006.01)
  *B29D 22/02* (2006.01)
  *B29L 22/02* (2006.01)

(52) U.S. Cl.
  CPC ...... *A61M 25/10* (2013.01); *A61M 25/10185* (2013.11); *A61M 29/02* (2013.01); *B29D 22/02* (2013.01); *A61M 25/1002* (2013.01); *A61M 2025/1045* (2013.01); *A61M 2025/1052* (2013.01); *A61M 2025/1056* (2013.01); *B29L 2022/022* (2013.01)

(58) Field of Classification Search
  CPC .......... A61M 25/1002; A61M 25/1011; A61M 25/10185; A61M 29/02; A61F 2/954; A61F 2/958; A61F 2/07; A61F 2/856; A61F 2002/067; A61F 2002/821; A61F 2002/065
  USPC .................. 623/1.11–1.54; 606/194
  See application file for complete search history.

(56) References Cited

U.S. PATENT DOCUMENTS 7,670,622 B2  3/2010  de Vries

| | | | |
|---|---|---|---|
| 2001/0011188 A1* | 8/2001 | Berry | A61F 2/91 623/1.16 |
| 2001/0020184 A1* | 9/2001 | Dehdashtian | A61F 2/07 623/1.16 |
| 2003/0139759 A1 | 7/2003 | Schaible et al. | |
| 2004/0210299 A1* | 10/2004 | Rogers | A61F 2/958 623/1.15 |
| 2004/0254602 A1* | 12/2004 | Lehe | A61F 2/013 606/200 |
| 2005/0010278 A1* | 1/2005 | Vardi | A61F 2/82 623/1.15 |
| 2005/0192656 A1 | 9/2005 | Eidenschink | |
| 2008/0288041 A1 | 11/2008 | Holman et al. | |
| 2009/0171430 A1* | 7/2009 | Baim | A61F 2/954 623/1.11 |
| 2011/0307047 A1* | 12/2011 | Bourang | A61F 2/856 623/1.11 |

FOREIGN PATENT DOCUMENTS

| | | |
|---|---|---|
| EP | 1369097 | 10/2003 |
| EP | 1435249 | 7/2004 |
| WO | 9508289 | 3/1995 |
| WO | 03074118 | 9/2003 |
| WO | 2007076463 | 7/2007 |

* cited by examiner

ARRANGEMENT FOR IMPLEMENTING KISSING BALLOONS FOR SIMULATING A BIFURCATED VESSEL, A KIT, A METHOD OF MANUFACTURING THE ARRANGEMENT AND A CATHETER PROVIDED WITH A BUFFER VOLUME

This application is the U.S. National Phase of, and Applicants claim priority from, International Patent Application Number PCT/NL2012/050863 filed 7 Dec. 2012, which claims priority from EP11192469.2 filed 7 Dec. 2011 and U.S. Provisional Application Ser. No. 61/567,706 filed 7 Dec. 2011, each of which is incorporated herein by reference.

FIELD OF THE INVENTION

The invention relates to an arrangement for implementing kissing balloons simulating a bifurcated vessel.

The invention further relates to a kit comprising the arrangement for implementing kissing balloons simulating a bifurcated vessel.

The invention still further relates to a method of manufacturing an arrangement for implementing kissing balloons for simulating a bifurcation.

The invention still further relates to a catheter comprising an inflatable balloon, a lumen arranged in fluid communication with the inflatable balloon and adapted for filling the said balloon with an inflation fluid provided via a port.

BACKGROUND OF THE INVENTION

An embodiment of an arrangement for enabling kissing balloons as is set forth in the opening paragraph is known from EP 1 369 097. In the known arrangement a balloon catheter assembly is provided having twin balloons adapted for treating bifurcated vessels. In the known system one or both balloons may be stepped to provide a proximal section, a distal section of larger diameter and a step between these two sections. In use, the twin balloons are positioned across the bifurcation so that the distal sections of the two balloons enter respectively the main and side branches distally of the bifurcation and the smaller diameter proximal sections are positioned side by side in the common area in the vessel proximally of the bifurcation.

It is a disadvantage of the known system that the said side by side positioning, although occasionally resulting in a common surface of the two balloons, is not reproducible. It will be further appreciated that in specific treatments of an abnormal bifurcated area, such as aneurism at bifurcation, a pre-defined and reproducible kissing surface of the two balloons is required.

SUMMARY OF THE INVENTION

It is an object of the invention to provide a balloon assembly suitable for simulating two bifurcated vessels wherein a kissing surface simulating the main lumen may be provided in a reliable and reproducible way.

To this end the arrangement for implementing kissing balloons simulating a bifurcated vessel, according to the invention, comprises a first catheter having a first inflatable balloon at or near its distal portion, a second catheter having a second inflatable balloon at or near its distal portion, wherein a holding element is provided on the said first balloon, the said holding element being adapted for:

i) allowing the distal portion of the second catheter to pass there through;
ii) affixing the second catheter in a proximal vicinity to the first catheter so that, in use, respective facing surfaces of the inflated first balloon and the inflated second balloon touch each other.

According to an aspect of the invention the first catheter is provided with a holding element which is dimensioned and shaped for holding and maintaining the second catheter and its balloon in a close proximity of the first catheter and its balloon. It will be appreciated that in general suitable balloons for introduction into an aneurism are about 7 F in diameter. Accordingly, this diameter is at least an order of magnitude smaller that a diameter of an inflated balloon. Therefore, when the second catheter is hold in proximity of the first catheter and when the respective balloons are inflated at their working pressure a kissing surface between these balloons will always be present. It will be appreciated that the configuration according to the invention may be further broadened to a system having two or more balloons. The balloons may be "dog-bone" shaped. However, substantially straight balloons may be used as well. It will be further appreciated that in practice, usually, a guidewire will be inserted through the holding element first, after which the second catheter may be guided through the holding element. The holding element may be provided on different portions of the first balloon. This aspect of the invention will be discussed in more detail with reference to FIG. 1.

It is found particularly advantageous to use the arrangement according to the invention for treating an aneurism, wherein the two balloons having a kissing surface are provided within the aneurism, the balloons further having their proximal regions propagating in the common vessel and their distal regions propagating in a respective bifurcated vessel. The thus simulated bifurcation is used to cooperate with a suitable filler, such as a polymer, for filling the aneurism thereby preventing its disruption. When the filler is hardened the balloons may be deflated and the catheters are withdrawn. The resulting passage within the filler is retained thereby providing a passage for blood within this bifurcation.

It will be appreciated that an embodiment of an arrangement having two balloons having a kissing surface is known US 2005/0192656. However, the known arrangement is adapted for enabling an introduction of a stent mounted on a balloon in a region of a vessel bifurcation. The known arrangement comprises a stepped balloon which has a first section of a first diameter and a second section of a second diameter. The first section is sized to deploy a first stent portion having a larger deployed diameter, while the second section is sized to deploy a second stent portion having a smaller diameter. It will be appreciated that when the first section and the second section are deployed a contact surface may occur between the corresponding balloons.

However, the arrangement known from US 2005/0192656 is not suitable for simulating a bifurcated vessel, especially within an aneurism.

In an embodiment of the arrangement according to the invention the holding element is substantially cylindrically shaped.

It is found that it is particularly convenient to provide a substantially cylindrically shaped holding element because the introduction of the second catheter into the holding element may be easily facilitated. In particular, when the holding element comprises a distal portion and a proximal portion situated along the first balloon, the holding element may taper from the proximal portion towards the distal portion. This embodiment is found particularly practical as a larger orifice is provided for the second catheter when introducing it into the holding element. The tapered distal portion of the holding element may be dimensioned in dependence of the longitudinal dimension of the inflated first balloon and/or the second balloon for enabling due and preferably firm kissing between the said balloons.

Preferably, the holding element is arranged within 5 cm from the distal end of the first catheter.

It is found that by arranging the holding element within 5 cm from the distal end of the first balloon, preferably at about 5 cm from the distal end of the first balloon a suitable spatial interrelation between the first balloon and the second balloon may be established. This approach works particularly well for similar dimensioned catheters and balloons which are substantially symmetrically adjoined with respect to the holding element.

In a further embodiment of the arrangement according to the invention a transversal dimension of the holding element is about 1 cm and wherein a longitudinal dimension of the holding element is about 1-5 cm.

It will be appreciated that a dimension of a holding element is a compromise between a very small dimension for allowing the first catheter and the second catheter to come into full contact and a relatively large dimension for effectuating an easy introduction of the second catheter into the holding element. It will be appreciated that for differently shaped balloons different rationale may apply for selecting a suitable length of the holding element. For example for the so-called "dog-bone" balloons the longitudinal dimension of the holding element may be about 30% of the total length of the "dog-bone" balloon. Preferably, in this case, the holding element is provided on the middle portion of the balloon, which has a reduced diameter. For the straight balloons the preferable longitudinal dimension of the holding element is about 25% of the total length of the straight balloon. For the straight balloon, the holding element may be provided at a median portion of the balloon.

It was found that a cross-sectional dimension of the holding element of about 1 cm provides a suitable compromise between these two extremes still enabling a pre-defined and reliable kissing surface emerging between the two inflated balloons.

It will be appreciated that the holding element is preferably flexible. This reduced the risk of lumen damage when introducing the first catheter intravascularly as well as improves handling during insertion of the second catheter into the first catheter.

In a still further embodiment of the arrangement according to the invention the holding element comprises a radiopaque marker.

Because the procedure of a catheter introduction is carried out under X-ray real-time imaging the catheter tips are generally provided with a radiopaque marker for visualization purposes. Accordingly, for simplifying location of the holding element on the first catheter the holding element may be advantageously provided with a radiopaque marker. It is possible that the radiopaque marker is dimensioned and configured for indicating the distal and the proximal part of the holding element, especially when the holding element extends along the body of the first balloon.

A kit, according to the invention for enabling in-vivo simulation of a bifurcated vessel comprises an arrangement as is set with regard to the foregoing and a shapeable material, preferably a polymer.

It will be appreciated that the shapeable material may be introduced in vivo or ex-vivo (for training purposes, for example) around the arrangement having durable kissing surfaces between the expanded balloons. When the shapeable material assumes is final shape and form the catheters may be extracted leaving a bifurcated lumen within the shapeable material.

The shapeable material may in principle be any biocompatible shapeable material. In particular suitable are polymer compositions comprising a physiologically acceptable (pre) polymer, such as polyurethane(pre)polymer or a silicone (pre)polymer.

Such compositions are known in the art per se. Suitable polyurethane(pre)polymer compositions are e.g. known from U.S. Pat. No. 7,670,622 or U.S. Pat. No. 6,306,177, which are incorporated herewith by reference as particular embodiment of the invention. Suitable silicone(pre)polymer compositions are e.g. known from EP-A 1 435 249 which is incorporated herewith by reference as a suitable embodiment of the invention. Further examples of shapeable polymer compositions include biopolymer compositions, e.g. as described in WO 95/08289 and epoxiresins, e.g. as described in EP 0 667 131 A2, which are incorporated herewith by reference.

Such compositions can be introduced in vivo in a fluid state and cured in vivo, to form an essentially solid structure.

Preferably, the polymer composition meets one, two or three of the following conditions:
  the (uncured) composition has a viscosity of 2 000 to 12 000 cSt at 25° C.
  the polymer composition is curable in the presence of a curing catalyst at 37° C. to form a cured material with an elongation until rupture of at least 5%, preferably at least 25%
  the polymer composition is curable in the presence of a curing catalyst at 37° C. to form a cured material with an elastic modulus of at least 1 MPa The viscosity as defined herein is the kinematic viscosity in cSt as measured by Brookfield viscosimeter(UK), model ND J-1 and/or rheometer RMS 800 from Rheometrics, USA. The kinematic viscosity of a fluid in cSt corresponds to the dynamic viscosity in mPa·s divided by the density of the fluid in $g/cm^3$.

The elongation until rupture is defined herein is the value as measured by a Zwick 1445 tensile strength tester (Germany).

The elastic modulus as defined herein is the value as measured by dynamic mechanical analyser, DMA 7 from Perkin-Elmer (USA).

Suitable polymer compositions having a viscosity of 2 000 to 12 000 cSt and/or being curable to form a cured material with an elongation until rupture of at least 5%, preferably at least 25%, and an elastic modulus of at least 1 MPa, are known from EP-A 1 435 249. The content of the publication is incorporated by reference, in particular with respect to details on the content of the composition and manners to administer the polymer composition to a body vessel and cure the composition.

Preferably the polymer composition comprises a polydialkylsiloxane (pre-) polymer, in particular a polydimethylsiloxane homo- or copolymer, having at least two vinyl groups, as described in EP-A 1 435 249. The contents hereof with respect to the polydialkylsiloxane (pre-) polymer, in particular paragraphs [0046]-[0048], are incorporated by reference In a particularly preferred embodiment, the polymer composition further comprises a filler and a curing agent. In particular, the filler and/or curing agent may be selected from those disclosed in EP-A 1 435 249. The contents hereof with respect to the filler and the curing agent, in particular paragraphs [0051]-[0067] are incorporated by reference.

The polymer composition may comprise one or more (further) additives, in particular one or more additives selected from the group of contrast agents, curing inhibitors and chain extenders, e.g. as described in EP-A 1 435 249, paragraphs [0069]-[0071], which paragraphs are incorporated herein by reference.

Further, a curing catalyst may be included. If the polymer composition is provided in a kit, the curing catalyst is preferably included in a separate container in the kit. The catalyst is then mixed with the polymer composition briefly before administering the composition in vivo. The catalyst preferably is a platinum complex, e.g. as described in EP-A 1 435 249, paragraphs [0075]-[0078], which paragraphs are incorporated herein by reference.

The method of manufacturing an arrangement for implementing kissing balloons for simulating a bifurcation according to the invention comprises the steps of:

providing a first catheter having a first inflatable balloon at or near its distal portion with a holding element arranged on the first balloon, said holding element being adapted for maintaining a second catheter having a second inflatable balloon at or near a distal portion of the second catheter in a proximal vicinity to the first catheter so that, in use, respective facing surfaces of the first inflated balloon and the second inflated balloon touch each other.

As has been mentioned earlier, there is a need of an assembly comprising a first catheter with a first balloon and a second catheter with a second balloon wherein upon inflation of the balloons a reliable and reproducible kissing surface there between is established. The method of manufacturing the arrangement as is set forth in the foregoing enables a configuration wherein the kissing surface between two balloons may easily and reliably be effectuated.

In an embodiment of the method according to an aspect of the invention the holding element is substantially cylindrically shaped. This is found to be advantageous as the second catheter during intravascular introduction thereof will travel substantially along the first catheter. The cylindrically shaped holding element can easily capture the tip of the approaching second catheter.

In a further embodiment of the method according to the invention the holding element comprises a distal portion and a proximal portion, and wherein the holding element tapers from the proximal portion towards the distal portion.

It is found that by allowing the proximal portion of the holding element to have a larger dimension than the distal portion of the holding element, first, an easy introduction of the second catheter can be achieved and, secondly, the second catheter may be held close to the first catheter as the tapering surface of the holding element will substantially define a line of approach for the second catheter.

In a still further embodiment of the method according to a further aspect of the invention the holding element is about 1-5 cm long and is preferably substantially centrally arranged along the length of the first balloon. However, it will be appreciated that the holding element may be arranged anywhere along the first balloon. It is found that these shape and location details are preferable for enabling a reliable and sustainable kissing surface between the two extended balloons.

A catheter comprising an inflatable balloon, a lumen arranged in fluid communication with the inflatable balloon and adapted for filling the said balloon with an inflation fluid provided via a port, the catheter further comprising a further port connectable to the said lumen, said further port comprising a buffer volume adapted to be filled with a gas for:

substantially equalizing an internal pressure in the lumen exhibited by the inflation fluid, and for allowing the fluid from the balloon to reflux by compressing the gas in the buffer volume upon deformation of the inflatable balloon.

This embodiment is based on the recognition that a substantial degree of deformation is desired for adaptation of the kissing surface between the balloons as well as between the balloon and the vessel wall after dilatation of the balloons. It is found that when the balloons are filed with the liquid to an extend that that a substantially rigid three-dimensional body is provided, the balloons have an inferior kissing surface with a small point-like contact surface area.

In accordance with an aspect of the invention, the balloon may be suitably deformable and compliable in use due to the reflux of the liquid into the second port so that a substantially flat contact area is enabled.

In accordance with an aspect of the invention a buffer volume is provided comprising a compressible medium, such as gas. The gas may be provided under a pressure for levelling the intraluminal fluid pressure within the catheter. However, upon an event the expanded balloon is handled and undergoes deformation, gas in the buffer volume may be advantageously compressed by a refluxing fluid from the balloon due to deformation and/or partial collapsing of the balloon.

In an embodiment of the catheter according to an aspect of the invention the catheter further comprises a valve for switching between the first port and the second port.

It is found to be particularly advantageous to provide simple switching between the fluid port for by-filling the balloon with the fluid or for extracting the fluid from the balloon and a gas port for leveling the fluid pressure with the gas pressure and allowing the fluid to reflux.

Those skilled in the art would readily appreciate that the valves and ports known per se in the art may be used. Accordingly, the construction of the valves and the ports will not be described in detail.

It will be appreciated that for one or both catheters of the arrangement for implementing kissing balloons simulating a bifurcated vessel as is set forth in the foregoing the catheter comprising a buffer-filled gas having a fluid port and a gas port as is set forth in the foregoing may be used.

It is found that introduction of the substantially deformable balloons into a bifurcation is substantially simplified and improved when the balloons may be depleted in use using reflux of the inner fluid into a buffer volume.

These and other aspects of the invention will be further discussed with reference to drawings which are provided for illustrative purposes only and may not be used for limiting the scope of the appended claims. In the Figures like reference numerals refer to the like elements.

DETAILED DESCRIPTION OF THE DRAWINGS

Figure 1:
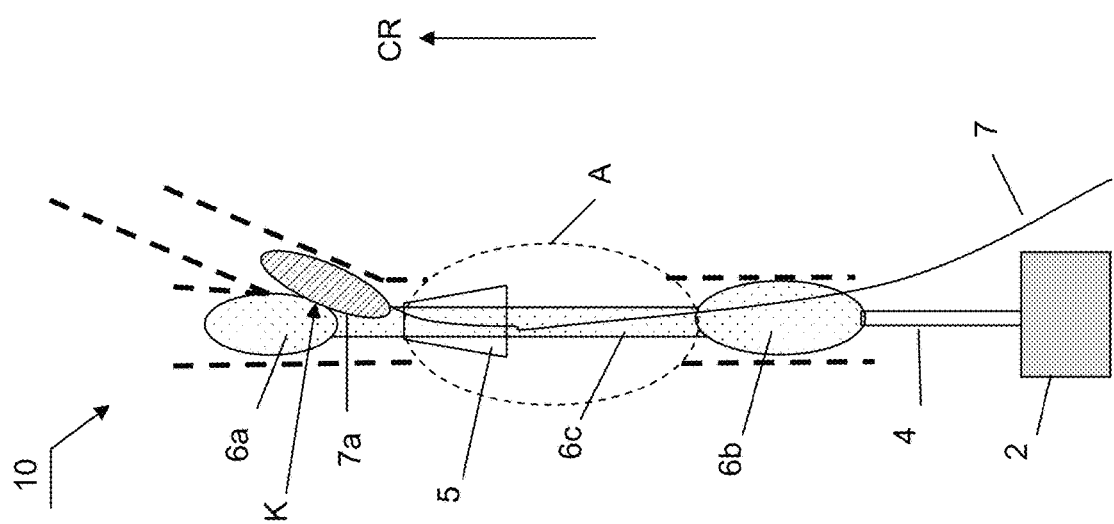
FIG. 1 present a schematic view of an embodiment of an arrangement for effectuating kissing balloons according to an aspect of the invention.

FIG. 1 present a schematic view of an embodiment of an arrangement for effectuating kissing balloons according to an aspect of the invention.

In the arrangement 10 a bifurcated vascular structure is shown, wherein the bifurcation extends in a cranial direction CR of a patient. An example of such a bifurcation is a bifurcation of a carotid artery.

In the arrangement 10 a first catheter 4 comprises a port 2 adapted to supply a suitable fluid for filling an internal lumen of the catheter 4 for expanding a balloon arranged at or near a distal portion of the catheter 4. The balloon may be a straight balloon having a substantially uniform diameter along its useful length. Alternatively, the balloon may refer to a so-called dog-bone balloon, comprising a first portion 6a, having an enlarged diameter, a central portion 6c having a reduced diameter and a second portion 6b having an enlarged diameter. In general, a physiologic salt solution may be used for the suitable filling fluid.

In order to simulate a vascular bifurcation, the first balloon is provided with a holding element 5 adapted to receive and to maintain a second catheter 7 in a direct vicinity of the first catheter 4 so that when a second balloon 7a is expanded a substantially permanent kissing surface is established between outer surfaces of the first balloon 6a and the second balloon 7a.

The arrangement 10 according to the invention is particularly suitable for treating an aneurism. For example, the dog-bone like balloon 6a, 6b, 6c may be maneuvered in such a way that the proximal balloon 6b dwells in a main lumen and the distal balloon 6a dwells in a bifurcated lumen. The medial portion of the balloon 6c may extend across an aneurism A. Then, the second catheter 7 is being positioned next to the first catheter 4 through the holding element 5 so that the second balloon 7a engages the first balloon 6a by a kissing surface K. After the kissing surface is established the aneurism may be treated, for example by filling it with a sheapeable polymer.

It will be appreciated that various embodiments of the holding element 5 may be envisaged. For example, the holding element may be provided as a substantially cylindrically shaped body, notably a substantially cylindrically shaped flexible body. Alternatively, the holding element may comprise one or more circular receptacles. The circular receptacles may be in the shape of individual rings or interconnected rings. Still alternatively, the holding element 5 may be provided as a hook-shaped body, preferably having a safety loop for avoiding that the second catheter disengages with the holding element in use.

In a particular embodiment, the holding element may be tapered from its proximal portion to its distal portion. It will be appreciated that the distal portion of the holding element is located closer to the catheter tip than the proximal portion of the holding element. By allowing the holding element 5 to taper a wider opening at the proximal portion of the holding element may be provided thereby simplifying insertion of the second catheter 7 through the holding element 5.

According to a still further embodiment of the arrangement according to the invention the holding element 5 covers about 25-30% of a longitudinal length of the first balloon having sub-portions 6a, 6b, 6c. Known balloons may be as large as 15 cm. The holding element, when implemented as a substantially cylindrically shaped body, may be about 1-5 cm long and may have an inner diameter of about 1 cm.

The holding element is preferably firmly attached on the middle portion of the balloon 6c not allowing the holding element 5 to move with respect to its mounting location. For example, the holding element 5 may be suitably glued to the balloon portion 6c.

Figure 2:
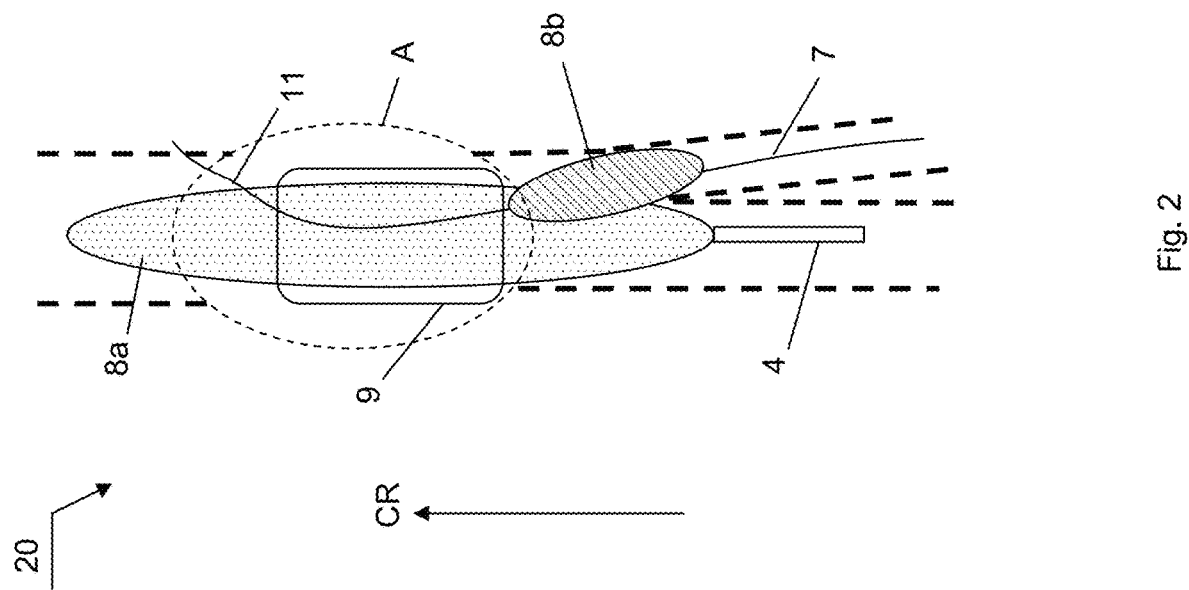
FIG. 2 presents a schematic view of a further embodiment of kissing balloons according to a further aspect of the invention.

FIG. 2 presents a schematic view of a further embodiment of kissing balloons according to a further aspect of the invention. In this arrangement the bifurcated vessels adjoin in the cranial direction CR of a patient. The kissing balloons 8a, 8b are embodied by a first extended balloon 8a corresponding to a first catheter 4 and a second extended balloon 8a corresponding to a second catheter 7. The second catheter may be guided by a guidewire 11. The first catheter 8a and the second catheter 8b are maintained in each other's vicinity by using a holding element 9 provided on the first balloon 8a. It will be appreciated that although in this embodiment a straight balloon is shown, it is also possible to use a dog-bone balloon, as explained with reference to FIG. 1.

Accordingly, in use, the second catheter 8a is maneuvered through the holding element 5 using a guide wire 11, wherein the second balloon 8a is preferably depleted, so that the second balloon 8a is at about the same position as the first balloon 8a. Afterwards, the second balloon 8a is inflated using a suitable fluid from a fluid supply port (not shown). It will be appreciated that the fluid supply port feeding the first catheter 4 and the fluid supply port feeding the second catheter are usually separated entities. However, it is possible that the catheter 4 and the catheter 7 are fed from a same of joined port.

In addition, it is noted that it is possible that the first balloon 8a and the second balloon 8b have different longitudinal dimensions. However, for simulating a vascular bifurcation, the first balloon 8a and the second balloon 8b may generally have substantially the same longitudinal dimension.

Upon an event the second balloon 8b is positioned properly with respect to the first balloon 8a, it may be inflated. As a result, the second balloon will come into a permanent contact with the first balloon 8a by forming a so-called kissing surface with it. It will be appreciated that a place where the balloons 8a, 8b adjoin may be determined by a position of the holding element 5. Generally, the balloons 8a, 8b may assume a kissing position near to their respective proximal regions.

It will be further appreciated that the balloons 8a, 8b are inflated to make a contact with an inner surface of the respective lumens shown in FIG. 2.

Figure 3:
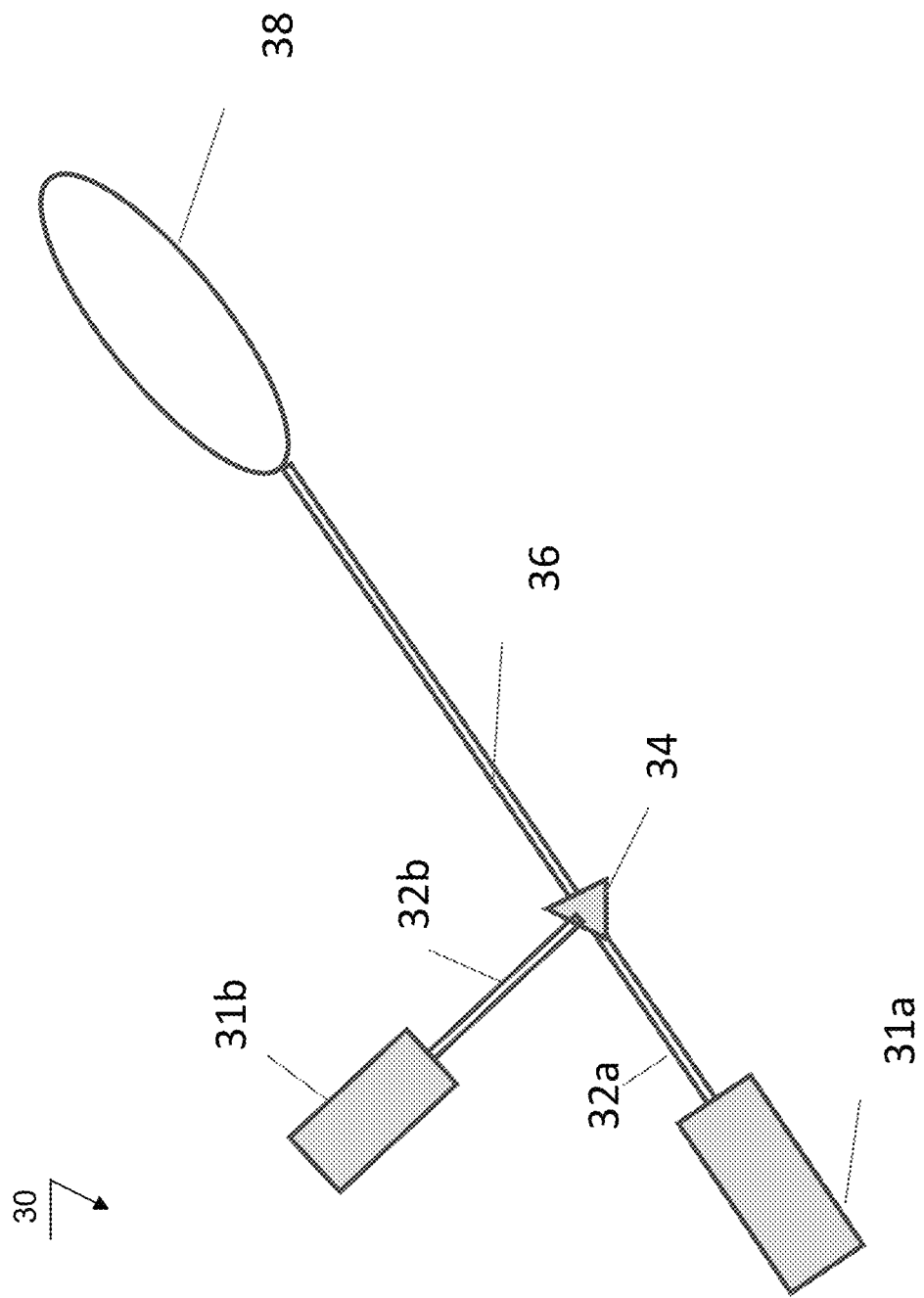
FIG. 3 presents a schematic view of a catheter comprising an inflatable balloon connected to a valve adapted for deforming the balloon in use.

FIG. 3 presents a schematic view of a catheter comprising an inflatable balloon connected to a valve adapted for deforming the balloon in use.

It will be appreciated that such catheter may be used for one or both catheters referred in FIG. 1 or 2.

The catheter 36 according to the present aspect of the invention comprises an inner lumen (not shown) adapted to supply a suitable inflation fluid into an extendable balloon 38 located at or near a distal portion of the catheter 36. The fluid is provided from a supply unit 31a via a port 32a.

In addition, the catheter 36 further comprises a second port 32b connected to the inner lumen of the catheter 36, said port being in fluid communication with a gas supply unit 31b.

It will be appreciated that the catheter 26 may be provided with two valves, each adapted to opening and closing its own port to the lumen of the catheter 36.

However, in a preferred embodiment, the catheter 36 may comprise a common valve 34 adapted to close and open two ports 32a, 32b in sequence. Accordingly, in use the valve 34 may be set into a first state by allowing the fluid from the fluid supply unit 31a to fill the balloon 38 at a suitable working pressure. Generally, the working pressure may be one or more atmospheres.

When it is desired that the inflated balloon increased its deformability and compliability, the fluid port may be closed by setting the valve into a second state for opening the port 32b. It will be appreciated that prior to this action the port 32b should be set at a pressure which is about the same as the inner pressure of the fluid inside the lumen of the catheter 36. For this purpose the gas supply unit 31b may be provided with a suitable pressure indicator.

When the pressure inside the gas port 32b equalized the pressure inside the balloon 38 it retains its shape. However, the inflated balloon is allowed to deform or partially collapse during further handling as the fluid from the balloon 38 may reflux into the gas buffer provided in the port 32b thereby compressing the gas. Accordingly, the balloon 38 may acquired a substantially increased compliance for bending, for example. It is found that such functionality of the inflated balloon is particularly advantageous for effectuating a good contact between the kissing balloons and between a balloon and an internal surface of the vascular lumen.

Figure 4:
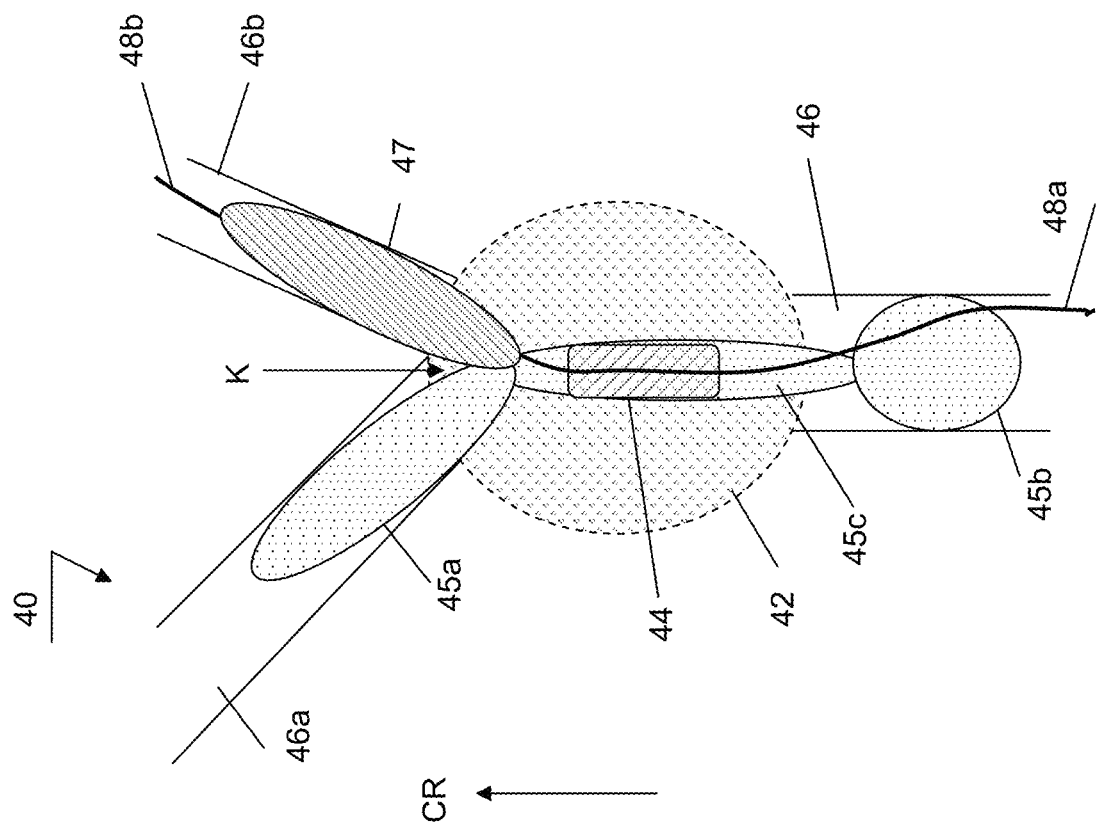
FIG. 4 presents in a schematic way an embodiment of a treatment of aneurism at a vascular bifurcation using the arrangement according to an aspect of the invention.

FIG. 4 presents in a schematic way an embodiment of a treatment of aneurism at a vascular bifurcation using the arrangement according to an aspect of the invention. For the sake of simplicity catheters having only one port are shown. However, it will be appreciated that one or both catheters having substantially improved deformation properties, as shown in FIG. 3, may be used as well.

In this particular embodiment a vessel 46 having two bifurcated arms 46a, 46b further exhibits an aneurism 42 proximal to the bifurcation. The bifurcated vessels 46a, 46b extend further in the cranial direction CR of a patient. In order to treat the aneurism 42, the arrangement according to the invention may be introduced via the main lumen 46, the aneurism 42 into the respective arms 46a, 46b.

It will be appreciated that the arrangement according to an aspect of the invention is preferably introduced step-wise. Accordingly, the first catheter comprising a dog-bone catheter having portions 45a, 45b, 45c and a holding element 44 is introduced into the first bifurcated arm 46a. For effectuating visualization of the progress of positioning of the first catheter, its distal tip may be provided with a radiopaque material, as known in the art.

When the first catheter is positioned inside the first bifurcated lumen 46a, having the first portion 45a located in a healthy region of a bifurcated vessel and a second portion 45b located in a healthy region of the main lumen 46, the balloon 45a, 45b, 45c may be inflated with a suitable inflation fluid from a port (not shown) so that the portions 45a, 45b engage an inner surface of the respective lumens. Next, the second catheter 48a is inserted into the second bifurcated vessel 46b via the holding element 44, preferably using a guidewire 48b. In order to enable visualization of the second catheter with respect to the patient's anatomy and the holding element, the tip of the second catheter may be provided with a suitable radiopaque structure and the holding element 44 may be provided with a suitable radiopaque identification. It is noted that in some embodiments radiopaque material may be provided on a proximal end of the holding element 44. However, it is also possible that both the proximal end and the distal end of the holding element 44 are provided with suitable radiopaque identifiers.

When the second catheter 48a has successfully passed the holding element 44, it is directed into the second bifurcated lumen 46b. Afterwards, the second balloon 47 is inflated from a fluid supply port (not shown) and forms a kissing surface K with a portion 45a of the first balloon.

It is found to be advantageous to provide the first catheter and the second catheter with respective gas buffers for increasing deformability and compliability of the respective balloons for improving their respective contact with each other and with the healthy portions of the lumen.

When the first balloon 45a and the second balloon 47 are properly positioned, their internal pressure may be suitably adapted to influence the dimension and the position of the kissing surface K therebetween.

Next, when the kissing surface is established, the inner volume of the aneurism 42 may be filled with a suitable shapeable material, such as a polymer, as is described with reference to the foregoing. After the polymer assumes its final shape and becomes shape-proof, the balloons 45a and 47 may be deflated and the catheters may be retracted. As a result the polymer filling the aneurism 42 exhibits an inner bifurcating opening simulating a vacular bifurcation due to the kissing balloons 45a, 47.

While specific embodiments have been described above, it will be appreciated that the invention may be practiced otherwise than as described. Moreover, specific items discussed with reference to any of the Figures may freely be inter-changed supplementing each other in any particular way. The descriptions above are intended to be illustrative, not limiting. Thus, it will be apparent to one skilled in the art that modifications may be made to the invention as described in the foregoing without departing from the scope of the claims set out below.

The invention claimed is:

1. An arrangement for implementing kissing balloons simulating a bifurcated vessel, comprising:
    a first catheter having a first inflatable balloon at or near a distal portion thereof, a second catheter having a second inflatable balloon at or near a distal portion thereof, wherein the first balloon comprises a holding element and the holding element being inseparably connected with the first balloon to prevent relative movement there between, the holding element being adapted for:
    (i) allowing the distal portion of the second catheter to pass there through;
    (ii) affixing the second catheter in a proximal vicinity to the first catheter so that, in use, respective facing surfaces of the first balloon and the second balloon touch each other when the first balloon and the second balloon are inflated.

2. The arrangement according to claim 1, wherein the holding element is substantially cylindrically shaped.

3. The arrangement according to claim 1, wherein the holding element comprises a distal portion and a proximal portion, and wherein the holding element tapers from the proximal portion towards the distal portion.

4. The arrangement according to claim 1, wherein the holding element is hook-like.

5. The arrangement according to claim 1, wherein the holding element is arranged within 5 cm from a distal end of the first balloon.

6. The arrangement according to claim 1 wherein a transversal dimension of the holding element is about 1 cm and wherein a longitudinal dimension of the holding element is about 1-5 cm.

7. The arrangement according to claim 1, wherein the holding element is flexible.

8. The arrangement according to claim 1, wherein the holding element comprises a radiopaque marker.

9. A kit, comprising the arrangement according to claim 1 and a shapeable polymer material.

10. A method of manufacturing an arrangement for implementing kissing balloons for simulating a bifurcation, the method comprising the steps of:
providing a first catheter having a first inflatable balloon at or near a distal portion of the first catheter, the first balloon comprising a holding element that is inseparably connected with the first balloon to prevent relative movement there between;
providing a second catheter having a second inflatable balloon at or near a distal portion of the second catheter, said holding element being adapted for allowing the distal portion of the second catheter to pass there through; and
affixing the second catheter in a proximal vicinity to the first catheter so that, in use, respective facing surfaces of the first balloon and the second balloon touch each other when the first balloon and the second balloon are inflated.

11. The method according to claim 10, wherein the holding element is substantially cylindrically shaped.

12. The method according to claim 10, wherein the holding element comprises a distal portion and a proximal portion, and wherein the holding element tapers from the proximal portion towards the distal portion.

13. The method according to claim 10, wherein the holding element is about 1-5 cm long and is preferably arranged within 5 cm proximally to the distal end of a first balloon.

14. A method for bridging an aneurysm in a bifurcated vessel using the arrangement according to claim 1.

15. An arrangement for implementing kissing balloons simulating a bifurcated vessel, comprising:
a first catheter having a first inflatable balloon at or near a distal portion thereof, a second catheter having a second inflatable balloon at or near a distal portion thereof, wherein the first balloon comprises a holding element and the holding element being inseparably connected with the first balloon to prevent relative movement there between before and after the first and second balloons have been inflated, wherein the first and second balloons are configured to contact an inner surface of a vascular lumen, and then deflated, the holding element being adapted for:
(i) allowing the distal portion of the second catheter to pass there through;
(ii) affixing the second catheter in a proximal vicinity to the first catheter so that, in use, respective facing surfaces of the first balloon and the second balloon touch each other when the first balloon and the second balloon are inflated.

16. The arrangement according to claim 1, wherein the holding element is fixedly secured to the first balloon by an adhesive.

* * * * *